United States Patent
Chapura et al.

(10) Patent No.: US 6,610,673 B1
(45) Date of Patent: *Aug. 26, 2003

(54) SOLID DOSE FORMS CONTAINING BISMUTH

(75) Inventors: Francis Bernard Chapura, Hamilton, OH (US); Daniel Louis Barone, Delhi, OH (US); Michael Gerard Colacino, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/328,879

(22) Filed: May 12, 1999

Related U.S. Application Data

(63) Continuation of application No. 08/217,524, filed on Mar. 24, 1994, now abandoned.

(51) Int. Cl.[7] ............... A61K 31/60; A61K 9/00; A61K 21/29; A61K 47/00
(52) U.S. Cl. ............. 514/159; 424/451; 424/464; 514/503; 514/769; 514/770; 514/772; 514/772.3; 514/777; 514/778; 514/779; 514/781; 514/784; 514/788; 514/867; 514/925; 514/960; 514/962; 514/975
(58) Field of Search ............... 424/464, 465, 424/617, 653, 451; 514/159, 503, 769, 770, 772, 772.3, 777, 778, 779, 781, 784, 788, 867, 925, 960, 962, 975

(56) References Cited

U.S. PATENT DOCUMENTS

| | | | | |
|---|---|---|---|---|
| 4,588,589 A | * | 5/1986 | Sheth et al. | 424/738 |
| 4,786,502 A | * | 11/1988 | Chapura et al. | 424/441 |
| 4,940,695 A | * | 7/1990 | Coveney et al. | 514/57 |
| 4,999,200 A | * | 3/1991 | Casillan | 424/480 |
| 5,192,752 A | * | 3/1993 | Chapura et al. | 514/152 |
| 5,244,670 A | * | 9/1993 | Upson et al. | 424/439 |
| 5,399,356 A | * | 3/1995 | Chapura et al. | 424/451 |

FOREIGN PATENT DOCUMENTS

| | | | |
|---|---|---|---|
| WO | WO 92/17164 | * | 10/1992 |
| WO | WO-93/09784 A1 | * | 5/1993 |

* cited by examiner

Primary Examiner—Jose' G. Dees
Assistant Examiner—Frank Choi
(74) Attorney, Agent, or Firm—Kelly L. McDow-Dunham; Betty J. Zsa; Karen F. Clark

(57) ABSTRACT

A swallowable, solid dose form composition for treating upper gastrointestinal tract distress containing bismuth subsalicylate, carbonate or bicarbonate salt, disintegrating agent, anionic or nonionic surfactant, and microcrystalline cellulose is described.

17 Claims, No Drawings

SOLID DOSE FORMS CONTAINING BISMUTH

CROSS REFERENCE TO RELATED APPLICATIONS

This application is a continuation of U.S. application Ser. No. 08/217,524, filed on Mar. 24, 1994, and abandoned in favor of this continuing application.

BACKGROUND OF THE INVENTION

Pink Pepto-bismol® liquid, which has bismuth subsalicylate as its active ingredient, is popular among consumers for quick relief of heartburn, indigestion, upset stomach, diarrhea, and nausea. Some consumers, though, do not like the taste or feel of such a liquid in their mouths, nor do they wish to chew a tablet with a similar taste, A swallowable tablet would be ideal for those consumers, but it is technically difficult to formulate and make a swallowable, bismuth-containing tablet which will give quick relief To be valued by consumers, such a tablet must break up quickly in the stomach so that the active ingredient is absorbed into the blood rapidly enough to provide quick relief. An especially preferred, swallowable, bismuth-containing solid dose form is one which provides relief from symptoms in about the same amount of time as liquid Pepto-bismol® takes to provide relief.

U.S. Pat. No. 5,225,197, Bolt et al, issued Jul. 6, 1993, describes a chewable tablet which includes a medicament in a chewable base such as mannitol and an effervescent couple such as citric acid-sodium bicarbonate.

U.S. Pat. No. 5,096,714, Kuhrts, issued Mar. 17, 1992 describes a prolonged dosage composition consisting essentially of a gel-forming dietary fiber, a biologically absorbable drug or other therapeutic agent, and certain disintegrants, namely, a physiologically acceptable edible acid and a mineral salt which release a physiologically acceptable gas upon ingestion.

SUMMARY OF THE INVENTION

The present invention relates to swallowable solid dose form compositions for treating upper gastrointestinal tract distress, comprising, by weight of the composition:

(a) from about 2% to about 25% of carbonate or bicarbonate salt;
(b) from about 0.5% to about 15% of disintegrating agent;
(c) from about 5% to about 70% of bismuth subsalicylate;
(d) from about 0.1% to about 3% of anionic or nonionic surfactant; and
(e) from about 15% to about 50% of microcrystalline cellulose.

The present invention further relates to a method for treating heartburn, indigestion, upset stomach, diarrhea, and/or nausea in humans or other mammals, the method comprising administering to a human or other mammal in need of such treatment a safe and effective amount of a pharmaceutical composition according to the present invention.

DESCRIPTION OF THE INVENTION

The swallowable, solid dose form compositions herein are comprised of (bi)carbonate salt, disintegrating agent, bismuth subsalicylate, anionic or nonionic surfactant, and microcrystalline cellulose, which are each described below. The present compositions preferably further comprise mannitol, silica, polyvinyl pyrrolidone, and other ingredients, which are also described below. The percentages given below are by weight of the composition unless otherwise indicated.

The swallowable (i.e. not chewable) solid dose form compositions herein preferably do not comprise a gel-forming dietary fiber such as psyllium, or an effervescent couple such as citric acid-sodium bicarbonate, or a physiologically acceptable edible acid and a mineral salt which release a physiologically acceptable gas upon ingestion. The present compositions are not prolonged dosage compositions; instead they are designed for quick dissolution in the stomach and absorption into the bloodstream. It is not necessary to include calcium chloride in the present compositions.

A. Carbonate or Bicarbonate Salt

The compositions herein comprise from about 2% to about 25%, preferably from about 5% to about 20%, most preferably from about 8% to about 15%, by weight of the composition, of carbonate and/or bicarbonate salt. Preferred are calcium, sodium, potassium, and/or magnesium salts of carbonate (most preferred) and/or bicarbonate. Most preferred is calcium carbonate. Without meaning to be bound by theory, it is believed that the calcium carbonate at this level is acting as a processing aid and is not included to impart effervescence to this swallowable solid dose form.

B. Disintegrating Agent

The compositions herein comprise from about 0.5% to about 30%, preferably from about 1% to about 20%, most preferably from about 2% to about 10%, by weight of the composition, of disintegrating agent.

The disintegrating agent is preferably selected from the group consisting of sodium starch glycolate, cross-linked polyvinyl pyrrolidone, croscarmellose sodium (a cross-linked cellulose), polyacrilin potassium (an ion exchange resin), alginic acid, starch, and mixtures thereof. The disintegrating agent is more preferably sodium starch glycolate or cross-linked polyvinyl pyrrolidone (available as Crospovidone), and is most preferably sodium starch glycolate (available as Explotab® from Edward Mendell Co.)

C. Bismuth Subsalicylate

The compositions herein comprise from about 5% to about 70%, preferably from about 10% to about 60%, most preferably from about 30% to about 50%, by weight of the composition, of bismuth subsalicylate. The average particle size of the bismuth subsalicylate (before incorporation with the remaining ingredients into the final form) is preferably from about 1 to about 50, more preferably from about 2 to about 30, most preferably from about 3 to about 10, microns. Without meaning to be bound by theory, this small particle size is believed to contribute to the efficacy of the solid dose forms herein by facilitating dissolution of the solid dose form in the stomach and allowing quicker absorption into the blood. Relief of symptoms is thus experienced rapidly, most preferably in an amount of time comparable to liquid Pepto-bismol®.

D. Anionic or Nonionic Surfactant

The compositions herein comprise from about 0.1% to about 3%, preferably from about 0.2 to about 1%, most preferably from about 0.4 to about 0.6%, by weight of the composition, of anionic and/or nonionic surfactant. Any anionic and nonionic surfactants, including synthetics, suitable for use in a swallowable solid dose form may be used in the present compositions.

Nonionic surfactants for use herein include compounds produced by the condensation of alkylene oxide groups (hydrophilic in nature) with an organic hydrophobic compound, which may be aliphatic or alkyl aromatic in nature. The surfactant is preferably a nonionic surfactant and is preferably selected from the group consisting of polyethylene oxide condensates of alkyl phenols; products derived from the condensation of ethylene oxide with the product resulting form the reaction of propylene oxide and ethylene diamine products; the condensation product of aliphatic alcohols having from 8 to 18 carbon atoms with ethylene oxide; long chain tertiary amine oxides corresponding to the following general formula wherein R1 contains an alkyl, alkenyl, or monohydroxy alkyl radical of from about 8 to about 18 carbon atoms, from 0 to about 10 ethylene oxide moieties, and from 0 to 1 glyceryl moiety, and R2 and R3 contain from 1 to about 3 carbon atoms and from 0 to about 1 hydroxy group; long chain tertiary phosphine oxides; and long chain dialkyl sulfoxides containing one short chain alkyl or hydroxy alkyl radical of from 1 to about 3 carbon atoms and one long hydrophobic chain which contain alkyl, alkenyl, hydroxy alkyl, or keto alkyl radicals containing from about 8 to about 20 carbon atoms, from 0 to about 10 ethylene oxide moieties, and from 0 to 1 glyceryl moiety; and mixtures thereof The most preferred surfactant for use herein is polyoxyethylene sorbitan monooleate.

Anionic surfactants for use herein include the alkali metal salts of organic sulfuric reaction products having in their molecular structure an alkyl radical containing from 8–22 carbon atoms and a sulfonic acid or sulfuric acid ester radical.

If the surfactant is an anionic surfactant, it is preferably selected from the group consisting of: the sodium, ammonium, potassium or triethanolamine alkyl sulfates, sodium coconut oil fatty acid monoglyceride sulfates and sulfonates, sodium or potassium salts of sulfuric acid esters of the reaction product of 1 mole of a higher fatty alcohol and 1 to 12 moles of ethylene oxide, sodium or potassium salts of alkyl pheno ethylene oxide per molecule and in which the alkyl radicals contain from 8 to 12 carbon atoms, sodium alkyl glyceryl ether sulfonates, the reaction products of fatty acids having from 10 to 22 carbon atoms esterified with isethionic acid and neutralized with sodium hydroxide, water soluble salts of condensation products of fatty acids with sarcosine, and mixtures thereof.

E. Microcrystalline Cellulose

The compositions herein further comprise from about 15% to 50%, preferably from about 20% to about 40%, most preferably from about 25% to about 35%, by weight of the composition, of microcrystalline cellulose. Preferred is Avicel ® PH102 microcrystalline cellulose NF from FMC Corp. (Philadelphia, Pa.). Preferably, the average particle size of the microcrystalline cellulose is from about 20 to about 200 microns, most preferably from about 80 to about 120 microns.

F. Optional Ingredients

The compositions herein preferably further comprise, by weight of the composition:
 (a) from about 2% to about 25%, preferably from about 5% to about 20%, most preferably from about 8% to about 15%, of soluble sugars and/or sugar alcohols, most preferably mannitol;
 (b) from about 0.02% to about 0.5%, preferably from about 0.05% to about 0.2%, most preferably from about 0.08% to about 0.15%, of silica, most preferably Cab-o-Sil® from Cabot Corp.;
 (c) from about 0.1% to about 5%, preferably from about 0.5% to about 2%, most preferably from about 0.6% to about 1.5%, of magnesium stearate; and
 (d) from about 0.5% to about 10%, preferably from about 1% to about 5%, most preferably from about 1.5% to about 3%, of polyvinyl pyrrolidone, most preferably Povidone®.

The soluble sugars are preferably selected from the group consisting of dextrose, sucrose, glucose, xylose, ribose, mannose, galactose, fructose, maltose, and mixtures thereof, and the sugar alcohols are preferably selected from the group consisting of xylitol, mannitol, sorbitol, and mixtures thereof Most preferred is mannitol.

Conventional ingredients of swallowable, solid dose forms, such as dye, may also be included herein.

A preferred composition herein comprises, by weight of the composition:
 (a) from about 8% to about 15% of calcium carbonate;
 (b) from about 2% to about 10% of sodium starch glycolate;
 (c) from about 3% to about 50% of bismuth subsalicylate;
 (d) from about 0.4% to about 0.6% of anionic or nonionic surfactant; and
 (e) from about 25% to about 35% of microcrystalline cellulose.

It preferably further comprises, by weight of the composition:
 (a) from about 5% to about 20% of mannitol;
 (b) from about 0.05% to about 0.2% of silica;
 (c) from about 0.1% to about 5% of magnesium stearate; and
 (d) from about 1% to about 5% of polyvinyl pyrrolidone.

G. Methods

The present invention further relates to a method for treating heartburn, indigestion, upset stomach, diarrhea, and/or nausea in humans or other mammals, the method comprising administering to a human or other mammal in need of such treatment a safe and effective amount of a pharmaceutical composition according to the present invention.

H. Form

The composition herein is preferably in the form of a tablet or capsule, more preferably in the form of a tablet shaped like a capsule. Conventional tablet/capsule making procedures are employed. Tablet hardness should be low enough to provide integrity and stability, but not so high as to interfere with dissolution of the tablet in the stomach.

The composition herein is preferably orally self-administered by humans and is preferably used for treating the same symptoms that liquid Pepto-bismol® is used to treat. The tablets/capsules are preferably taken by mouth to relieve heartburn, indigestion, upset stomach, diarrhea, and/or nausea in humans or other mammals. A composition herein is preferably orally administered for treatment of acid indigestion, heartburn or sour stomach.

Preferably, two caplets of about 675 milligrams per caplet (which includes approximately 262 milligrams of bismuth subsalicylate per caplet) are taken with water every ½ to 1 hour as needed up to a maximum of 8 doses in a 24 hour period (adult dose). The recommended dose for children 9–12 years of age is one caplet, for children 6–9 years of age is ⅔ caplet, for children 3–6 years of age is ⅓ caplet. Children under 3 should see a physician.

The following examples illustrate the compositions and processes of the present inventions. They are presented by way of example only and are not to be construed as limiting the scope of these inventions. It will appear to those of ordinary skill in the art upon reviewing the modifications described herein that various additional, related modifications may be made. Such modifications are intended to be within the scope of this invention.

All parts, percentages and ratios herein are by weight unless otherwise indicated. All references cited herein are expressly incorporated by reference.

EXAMPLE I

Swallowable Caplet

A swallowable caplet composition of the present invention is as follows.

| Ingredient | milligrams/caplet |
| --- | --- |
| Bismuth subsalicylate | 262.5 |
| Microcrystalline cellulose, NF[1] | 213.3 |
| Calcium carbonate | 67.5 |
| Mannitol | 67.5 |
| Sodium starch glycolate[2] | 40.5 |
| Polyvinyl pyrrolidone[3] | 13.5 |
| Magnesium stearate, NF | 5.4 |
| Polysorbate 80[4] | 3.4 |
| Silica[5] | 0.7 |
| Dye | 0.7 |
| Total | 675.0 |

[1]Available as Avicel ® PH102 from FMC Corp.
[2]Available as Explotab ® from Edward Mendell Co.
[3]Available as Povidone ®
[4]Available as Tween ® 80
[5]Available as Cab-o-Sil ® from Cabot Corp.

Preferably, the ingredients are added to a mixer, preferably a Processall (made by Processall of Cincinnati, Ohio) or a Littleford (made by Littleford of Kentucky) in the following order: part of the microcrystalline cellulose, the calcium carbonate, part of the sodium starch glycolate, the Polysorbate 80, the dye, and the bismuth subsalicylate. After the addition of the bismuth subsalicylate and mixing at high shear, the mixture is dried at 86° C. (187° F.) in the Processall to less than 2% moisture. Additional powders (microcrystalline cellulose, sodium starch glycolate, mannitol and polyvinyl pyrrolidone) are added, and granules are formed by spraying water (approximately 10% by weight of the composition) onto the mixture under high shear in the Processall. After additional drying, still in the Processall, to less than 3% moisture, silica (glidant) and magnesium stearate (lubricant) are added and mixed for about one minute. Caplets are then formed on a rotary tablet press. Two caplets of about 675 milligrams per caplet are taken with water every ½ to 1 hour as needed up to a maximum of 8 doses in a 24 hour period (adult dose).

This composition can alternatively be compressed into tablet or capsule form. Alternative ingredients disclosed in this specification can be substituted for the above ingredients. The amounts of these ingredients can be varied within the ranges specified herein.

EXAMPLE II

Swallowable Tablet

A swallowable tablet composition of the present invention is as follows.

| Ingredient | milligrams/tablet |
| --- | --- |
| Bismuth subsalicylate | 262.5 |
| Microcrystalline cellulose | 186.5 |
| Calcium carbonate | 15.0 |
| Croscarmellose sodium | 10.0 |
| Polyvinyl pyrrolidone | 20.0 |
| Magnesium stearate | 5.0 |
| Polysorbate 80 | 1.0 |

Ingredients are mixed under high shear according to Example I. The disintegrating agent here is Croscarmellose sodium. Tablets are formed using a rotary tablet press.

What is claimed is:

1. A swallowable, solid dose form composition for treating upper gastrointestinal tract distress comprising, by weight of the composition:
    (a) from about 2% to about 25% of carbonate or bicarbonate salt;
    (b) from about 0.5% to about 30% of disintegrating agent;
    (c) from about 30% to about 50% of bismuth subsalicylate;
    (d) from about 0.1% to about 3% of anionic or nonionic surfactant; and
    (e) from about 20% to about 40% of microcrystalline cellulose;
wherein the composition is free of: 1) a gel-forming dietary fiber; and 2) an effervescent couple of a physiologically acceptable edible acid and a mineral salt which releases a physiologically acceptable gas upon ingestion.

2. The composition according to claim 1 wherein the disintegrating agent is selected from the group consisting of sodium starch glycolate, cross-linked polyvinyl pyrrolidone, croscarmellose sodium, polyacrilin potassium, alginic acid, starch and mixtures thereof.

3. The composition according to claim 2 wherein the surfactant is a nonionic surfactant selected from the group consisting of polyethylene oxide condensates of alkyl phenols; products derived from the condensation of ethylene oxide with the product resulting from the reaction of propylene oxide and ethylene diamine products; the condensation product of aliphatic alcohols having from 8 to 18 carbon atoms with ethylene oxide; long chain tertiary amine oxides corresponding to the following general formula

wherein R1 contains an alkyl, alkenyl, or monohydroxy alkyl radical of from about 8 to about 18 carbon atoms, from 0 to about 10 ethylene oxide moieties, and from 0 to 1 glyceryl moiety, and R2 and R3 each contain from 1 to about 3 carbon atoms and from 0 to about 1 hydroxy group; long chain tertiary phosphine oxides; and dialkyl sulfoxides containing one short chain alkyl or hydroxy alkyl radical of from 1 to about 3 carbon atoms and one long hydrophobic chain which contains alkyl, alkenyl, hydroxy alkyl, or keto alkyl radicals containing from about 8 to about 20 carbon atoms, from 0 to about 10 ethylene oxide moieties, and from 0 to 1 glyceryl moiety; and mixtures thereof.

4. The composition according to claim 3 wherein the anionic or nonionic surfactant is polyoxyethylene sorbitan monooleate.

5. The composition according to claim 4 wherein the polyoxyethylene sorbitan monooleate is present at a level from about 0.4% to about 0.6%, by weight of the composition.

6. The composition according to claim 2 wherein the disintegrating agent is sodium starch glycolate or cross-linked polyvinyl pyrrolidone.

7. The composition according to claim 6 wherein the disintegrating agent is sodium starch glycolate and is present at a level from about 1% to about 20%, by weight of the composition.

8. The composition according to claim 1 further comprising from about 0.02% to about 0.5%, by weight of the composition, of silica.

9. The composition according to claim 1 in the form of a tablet or capsule.

10. The composition according to claim 9 in the form of a tablet shaped like a capsule.

11. The composition according to claim 1 further comprising from about 2% to about 25%, by weight of the composition, of soluble sugar selected from the group consisting of dextrose, sucrose, glucose, xylose, ribose, mannose, galactose, fructose, maltose and mixtures thereof.

12. The composition according to claim 11 further comprising from about 0.5% to about 10%, by weight of the composition, of polyvinyl pyrrolidone.

13. The composition according to claim 12 further comprising from about 2% to about 25%, by weight of the composition, of sugar alcohols selected from the group consisting of xylitol, mannitol, sorbitol, and mixtures thereof.

14. The composition according to claim 13 further comprising from about 0.1% to about 5% magnesium stearate.

15. The composition according to claim 1 comprising, by weight of the composition:

(a) from about 8% to about 15% of calcium carbonate;

(b) from about 2% to about 10% of sodium starch glycolate;

(c) from about 30% to about 50% of bismuth subsalicylate;

(d) from about 0.4% to about 0.6% of anionic or nonionic surfactant; and (e) from about 25% to about 35% of microcrystalline cellulose.

16. The composition according to claim 15 wherein the composition further comprises, by weight of the composition:

(f) from about 5% to about 20% of mannitol;

(g) from about 0.05% to about 0.2% of silica;

(h) from about 0.1% to about 5% of magnesium stearate; and (i) from about 1% to about 5% of polyvinyl pyrrolidone.

17. A method for treating at least one of heartburn, indigestion, upset stomach, diarrhea, and nausea in humans or other mammals, the method comprising administering to a human or other mammal in need of such treatment a safe and effective amount of a composition according to claim 1.

* * * * *